United States Patent [19]

King et al.

[11] Patent Number: 5,162,560

[45] Date of Patent: Nov. 10, 1992

[54] OLEFINIC AND ACETYLENIC AZASILACYCLOPENTANES

[75] Inventors: Russell K. King, Beaver Township, Bay County; Chi-long Lee, Midland, both of Mich.

[73] Assignee: Dow Corning Corporation, Midland, Mich.

[21] Appl. No.: 842,914

[22] Filed: Feb. 28, 1992

Related U.S. Application Data

[62] Division of Ser. No. 656,540, Feb. 15, 1991.

[51] Int. Cl.$^5$ .............................. C07F 7/08; C07F 7/18
[52] U.S. Cl. ................................... 556/445; 556/488
[58] Field of Search .......................... 556/445, 488

[56] References Cited

U.S. PATENT DOCUMENTS

| | | | |
|---|---|---|---|
| 3,146,250 | 3/1964 | Speier | 260/448.2 |
| 3,231,594 | 1/1966 | Speier | 556/488 X |
| 4,053,496 | 10/1977 | Föry et al. | 556/488 X |
| 4,053,497 | 10/1977 | Föry et al. | 556/448 X |
| 4,578,492 | 1/1986 | Pratt et al. | 556/407 |
| 4,584,393 | 4/1986 | Webb et al. | 556/407 |
| 4,659,852 | 4/1987 | Shinohara et al. | 556/488 X |
| 4,804,771 | 3/1989 | Pepe | 556/407 |
| 4,864,027 | 9/1989 | Shubert et al. | 556/445 X |
| 4,985,577 | 1/1991 | Shinohara et al. | 556/445 |
| 5,049,688 | 6/1991 | King et al. | 556/407 |
| 5,057,549 | 10/1991 | Herzig et al. | 556/445 X |
| 5,068,387 | 11/1991 | Kleyer et al. | 556/445 X |
| 5,118,772 | 6/1992 | Herzig et al. | 556/445 X |

Primary Examiner—Paul F. Shaver
Attorney, Agent, or Firm—Roger H. Borrousch

[57] ABSTRACT

Azasilacyclopentanes of the general formula

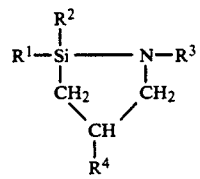

are prepared by reacting a dialkoxyalkyl(3-chloro-2-alkylpropyl)silane with a Grignard reagent of the formula $R^1MgBr$ in the presence of an ether, to make an alkoxyalkylalkenyl(3-chloro-2-alkylpropyl)silane which is reacted with acetyl chloride and a Lewis acid to make chloroalkylalkenyl(3-chloro-2-alkylpropyl)silane which is then reacted with an amine of the formula $R^3NH_2$ to make the azasilacyclopentanes.

4 Claims, No Drawings

OLEFINIC AND ACETYLENIC AZASILACYCLOPENTANES

This is a divisional of copending application(s) Ser. No. 07/656,540 filed Feb. 15, 1991.

BACKGROUND OF THE INVENTION

1. Field of the Invention

This invention relates to azasilacyclopentanes and a method of preparing it. This invention also relates to specific intermediate compounds, methoxymethylvinyl(3-chloro-2-methylpropyl)silane and chloromelthylvinyl(3-chloro-2-methylpropyl)silane.

2. Background Information

A search for new crosslinkers for use in the preparation of room temperature vulcanizing silicones (RTV's) lead to the discovery of the azasilacyclopentanes of the present invention. Speier in U.S. Pat. No. 3,146,250, issued Aug. 25, 1964, disclosed nitrogen-containing cyclic silanes and their preparation, which is hereby incorporated by reference to show the preparation of the nitrogen-containing cyclic silanes. Speier teaches nitrogen-containing cyclic silanes of the general formula

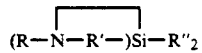

wherein R is a hydrogen atom, a monovalent hydrocarbon radical, a monovalent hydrocarbon radical containing divalent oxygen in the form of an ether linkage, an aminoalkyl radical, an aminophenyl radical, a halogenphenyl radicals, and an organosilyl radical of the general formula $(XR)Y_2Si-$ in which Y is a monovalent hydrocarbon radical and X is chlorine, bromine or iodine, R' is a divalent hydrocarbon radical with 3 to 6 carbon atoms between the bonds with the nitrogen atom and the silicon atom, R" is a monovalent hydrocarbon radical, a monovalent hydrocarbon radical with divalent oxygen as an ether linkage, an alkoxy radical, an alkoxy radical containing divalent oxygen as an ether linkage, and a phenoxy radical. Speier teaches preparing these compounds by reacting a halogeno-alkylhalogenosilane of the formula

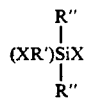

with an amino compound of the formula $RNH_2$. Speier also discloses making siloxanes having the unit formula

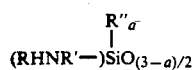

by hydrolyzing and condensing a compound of the formula

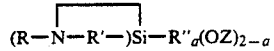

where Z is an alkyl radical, a phenyl radical, or an alkyl radical containing divalent oxygen in the form of ether linkages, and a is 0 to 2. Speier also teaches making endblocked diorganosiloxanes by effecting a reaction between

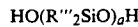

and

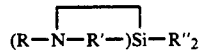

to produce a siloxane of the formula

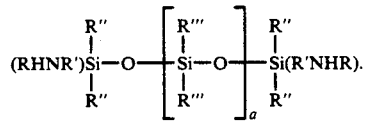

THE INVENTION

This invention relates to an azasilacyclopentane of the general formula

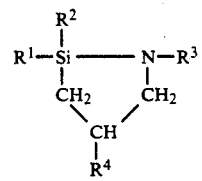

in which each of $R^1$, $R^2$, $R^3$, and $R^4$ is independently selected from the group consisting of a hydrogen atom and a monovalent hydrocarbon radical, where one of $R^1$, $R^2$, and $R^3$ is a monovalent hydrocarbon radical with olefinic unsaturation or acetylenic unsaturation. The monovalent hydrocarbon radicals include methyl, ethyl, propyl, butyl, phenyl, vinyl, allyl, hexenyl, cyclohexyl, tolyl, and isopropyl. Preferably, $R^1$, $R^2$, or $R^3$, when an olefinically or acetylenically unsaturated monovalent hydrocarbon radical, is olefinic and either vinyl or allyl.

The azasilacyclopentanes of the present invention can be prepared from an dialkoxy(chloroalkyl)silane of the general formula

(I)

where $R^5$ is an alkyl radical of from 1 to 5 carbon atoms per molecule, including methyl, ethyl, propyl, isopropyl, butyl, isobutyl, and pentyl, by first making a monoalkoxyalkylalkenyl-(3-chloro-2-alkylpropyl)silane of the general formula

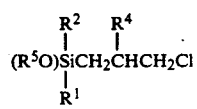

(II)

by reacting silane (I) with a Grignard reagent of the general formula $R^1MgBr$ in the presence of a solvent such as diether ether, tetrahydrofuran, or a mixture thereof. One preferred monoalkoxyalkylalkenyl(3- chloro-2-alkylpropyl)silane is methoxymethylvinyl(3-chloro-2-methylpropyl)silane. After the silane (II) is obtained, it can be reacted with acetyl chloride in the presence of a Lewis acid, preferably ferric chloride to make a chloroalkylalkenyl(3-chloro-2-alkylpropyl)silane of the general formula

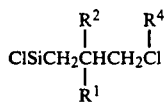
(III)

One preferred chloroalkylalkenyl(3-chloro-2-alkylpropyl)silane is chloromethylvinyl(3-chloro-2-methylpropyl)silane.

The azasilacyclopentanes of the present invention can be made by a process described by Speier where a halogenoalkylhalogenosilane of the formula

is reacted with an amino compound of the formula $RNH_2$. The present invention relates to making azacyclopentanes from specific chloroalkylalkenyl(3-chloro-2-alkylpropyl)silanes (formula III) which are new compounds. Speier is hereby incorporated by reference to show the known general reaction of chlorosilanes with an amino compound to make certain nitrogen-containing compounds as described herein.

These azasilacyclopentanes are useful for making polyorganosiloxanes which have reactive endgroups in the presence of moisture and do not produce leaving groups upon reaction.

The following examples are presented for illustrative purposes and should not be construed as limiting the present invention which is properly delineated in the claims. In the following examples, Me=methyl and Vi=vinyl.

EXAMPLE 1

1,2,4-Trimethyl-1-vinyl-2-aza-silacyclopentane was prepared. To a solution of 50.0 g (254 mmol) of dimethyoxymethyl(3-chloro-2-methylpropyl)silane in 250 ml of diethyl ether in a three-necked, 1 L (liter) round-bottom flask fitted with a mechanical stirrer, nitrogen inlet, and addition funnel was added over a one hour period, a solution of 290 ml (290 mmol) of 1M (molar) vinyl magnesium bromide in tetrahydrofuran (THF). The reaction was allowed to stir overnight under a nitrogen atmosphere at room temperature and the slightly yellowish liquid was decanted from the solids. The solvents were removed at 40° C. and 9 mmHg to yield 68.09 g of a yellow liquid with considerable amounts of solids. To this was added 50 ml of benzene and the salts were removed by filtration through a course glass frit funnel. The collected solids were washed with two 30 ml portions of benzene. The combined organic fractions were stripped at 50° C. and 9 mm Hg to yield 40.19 g of liquid with a small amount of salts. The results of gas chromatography-mass spectroscopy (GC-MS) showed the following composition of the liquid:

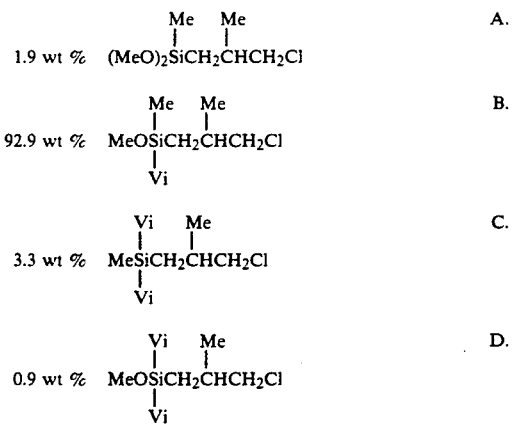

3.1 wt % of 9 unidentified impurities at an order of magnitude lower level.

The mass spectra was used to identify these compounds and the results were:

For B compound: 192, not observed, $M^+$; 165(10) M-Vi; 137 (10),NA; 121(210), $(MeO)ViClSi^+$; 109(230), $(MeO)MeClSi^+$; 101(780), $(MeO)MeViSi^+$; 56(1000), $C_4H_8^+$, where data are presented as charge(m/e), (relative intensity).

For C compound: 188, not observed, $M^+$; 161(8) M-Vi; 117 (280), $Vi_2ClSi^+$; 105(284), $MeViSi^+$; 97(489), $Vi_2MeSi^+$; 56(1000), $C_4H_8^+$.

For D compound: 204, not observed, $M^+$; 177(10), M-Vi; 121 (290), $(MeO)ViClSi^+$; 113(620), $(MeO)Vi_2Si^+$; 56(1000), $C_4H_8^+$.

The $^{29}Si$ nuclear magetic resonance(NMR) had one major peak at 6.63 ppm relative to tetramethylsilane. The crude product was purified by short path distillation. The fraction boiling at 75° C. at 6 mm Hg weighed 28.22 g (58% yield) and was compound B, methoxymethylvinyl(3-chloro-2-methylpropyl)silane.

Chloromethylvinyl(3-chloro-2-methylpropyl)silane was prepared. A mixture of 28.00 g (143.3 mmol) of compound B in 15.5 ml (17.10 g, 217.9 mmol, 1.5 eq) of acetyl chloride was allowed to sit at ambient temperature for 12 hours. A slight exotherm was noted. The low boiling material was removed by distillation and the product distilled at 88° C. to 90.5° C. and 30 mm Hg to give 25.2 g of material (88% yield). The product was chloromethylvinyl(3-chloro-2-methylpropyl)silane as was identified by $^{13}C$ NMR: 134.79 and 134.73 and 134.68 (1:2:1, 1.67), SiVi; 52.93 (1.00), $CH_2Cl$; 31.51 and 31.48 (0.83, CH; 22.88 and 22.84 (0.97), CHMe; 20.13 and 20.10 (1.01), $SiCH_2$; 0.59 and 0.54 (0.68), SiMe and by $^{29}Si$ NMR: 17.81 and 17.78 (1:1), where data are presented as ppm, (relative intensity).

1,2,4-Trimethyl-1-vinyl-2-aza-silacyclopentane was prepared. Methylamine was condensed into a 1 L round-bottom flask and distilled from sodium. To 490 ml (340 g, 11 mol) of methylamine was slowly added 309.8 g (1.57 mol) of chloromethylvinyl(3-chloro-2-methylpropyl)silane, which resulted in two phases. The two phase system was transferred to a Parr reactor and heated at 110° C. and 230 psig for 10 hours. The reaction mixture was cooled to −10° C., transferred to a 2 L round-bottom flask and 400 ml of cold pentane was added. The layers were separated, and the upper organic phase concentrated. After concentration, some ammonium salts had precipitated. These salts were removed by filtration and the product purified by distillation at reduced pressure to yield about 160 g (60% yield) of cyclic silazane with a small amount of ammonium salts. The distilled product was 97% pure 1,2,4-Trimethyl-1-vinyl-2-aza-silacyclopentane with two major higher boiling impurities (about 1 wt % each) and numerous minor higher boiling impurities. The GC-MS data was: 1,2,4-Trimethyl-1-vinyl-2-aza-silacyclopentane, Retention Time 2.00 min; 155 (365), M+; 154 (243), M+-H; 140(97), M+-Me; 126 (113), M+-Vi; 113 (962), M+-$C_3H_7$; 112 (1000), M+-$C_3H_7$; 89 (396), MeViSiN=$CH_2$+; 71 (465) MeViSiH+. The $^{13}C$ NMR spectra (ppm) was: 138.23 and 137.98, terminal vinyl; 132.86 and 137.98, internal vinyl; 62.19 and 61.92, N—$CH_2$; 33.93 and 33.80, methine; 32.09 and 32.06, NMe; 21.48 and 21.54, CHMe; 21.23 and 20.95 Si—$CH_2$; −3.43 and −4.29, SiMe. The $^{29}Si$ NMR had peaks at 6.229 and 6.039 relative to tetramethylsilane.

EXAMPLE 2

1,1,4-Trimethyl-2-allyl-2-aza-silacyclopentane was prepared. Chlorodimethyl(3-chloro-2-methylpropyl)silane (100 g, 0.54 mol) was slowly added to 211.73 g (3.71 mol, 6.87 eq) of undistilled allyl amine resulting in an exothermic reaction. This reaction mixture was stirred at room temperature for 15 hours, heated to reflux at atmospheric pressure for 72 hours, and heated to 120° C. under about 50 psig pressure for 16 hours. The following GC-MS ratios shown in Table I exemplified the reactions progression and the spectra observed were as shown.

TABLE I

| RETENTION TIME, MIN | 15 HOURS 20° C. | 24 HOURS REFLUX | 72 HOURS REFLUX | 16 HOURS 120° C. | COMPOUND |
|---|---|---|---|---|---|
| 2.70 | 0.0 | 3.9 | 21.3 | 71.9 | E |
| 2.82 | 0.0 | 1.0 | 1.1 | 0.9 | F |
| 3.20 | 50.4 | 11.0 | 4.1 | 0.0 | G |
| 5.19 | 29.5 | 63.0 | 40.2 | 0.0 | H |
| 8.46 | 20.0 | 8.8 | 8.1 | 2.4 | I |
| 9.58 | 0.0 | 9.3 | 10.1 | 6.1 | J |
| 10.58 | 0.0 | 3.1 | 15.1 | 18.7 | K |

Compound E was 1,1,4-trimethyl-2-allyl-2-aza-silacyclopentane and the spectra was 169 (819), M+; 154 (1326), M+-$CH_3$; 142 (1074), M+-Vi; 127 (375), M+-$C_3H_6$; 126 (354), M+-$C_3H_7$; 100 (784), M-69; 86 (8734), $Me_2SiN$=$CH_2$+; 59 (10000), $Me_2SiH$+. Compound F not determined.

Compound G was chlorodimethyl(3-chloro-2-methylpropyl)silane and the spectra was 184 (0), M+; 169 (233), M+-Me; 137 (292), M+-47; 113 and 115 (2459 and 1991), $Cl_2MeSi$+; 93 (9786), $ClMe_2Si$+; 56 (10000), $C_4H_8$.

Compound H was allylaminodimethyl(3-chloro-2-methylpropyl)silane and the spectra was 205 (10), M+; 190 (79), M+-Me; 170 (153), M+-Cl; 149 (618), M+-$C_4H_8$; 134 and 136 (1263 and 508), M+-$CH_3$—$C_4H_8$; 120 and 122 (1250 and 625), unassigned; 114 (10000), $CH_2$=$CHCH_2NHSiMe_2$+; 98 (4709), unassigned; 93 and 95 (4999 and 1948), $ClMe_2Si$+.

Compound I was 1,1,3,3-tetramethyl-1,3-bis(3-chloro-2-methylpropyl)disiloxane and the spectra was 314 (0), M+; 187 and 189 (2045 and 1291), $ClMe_2SiOSiMeCl$+; 167 and 169 (10000 and 3897), $ClMe_2SiOSiMe_2$+.

Compound J was 1,1,3,3-tetramethyl-1-(3-chloro-2-methylpropyl)-1-(3-allylamino-2-methylpropyl)disiloxane and the spectra was 335 (0), M+; 320 (52), M+-Me; 167 and 169 (1216 and 463), $ClMe_2SiOSiMe_2$+; 70 (10000), $CH_2$=$CHCH_2NH$=$CH_2$+.

Compound K was 1,1,3,3-tetramethyl-1,3-bis(3-allylamino-2-methylpropyl)disiloxane and the spectra was 356 (0), M+; 170 (1017), $CH_2$=$CHCH_2NHCH_2CH(CH_3)CH_2SiMe_2$+; 169 (1177), peak 170-H; 70 (10000), $CH_2$=$CHCH_2NH$=$CH_2$+.

Upon cooling the product of the reaction, a two phase system resulted. The upper phase weighed 111.85 g and contained most of the product 1,1,4-trimethyl-2-allyl-2-aza-silacyclopentane. The lower phase weighed 177.12 g and was an amber viscous liquid. This lower phase was concentrated at atmospheric pressure with a pot temperature of 120° C. to 122 g. Another 4.0 g of the upper phase was separated upon cooling. The combined product phases were distilled under vacuum. After a slow evolution of allylamine, the product codistilled with an ammonium salt at 78° C. and 30 mmHg. Filtration gave 51.63 g (56% yield) of essentially pure 1,1,4-trimethyl-2-allyl-2-aza-silacyclopentane. The $^{13}C$ NMR was: 138.13, vinyl; 114.39, vinyl; 58.98, allyl $CH_2$; 50.31, ring $CH_2N$; 31.88, CH; 21.94 and 21.50, $SiCH_2$ and C—Me; 0.22 and −0.76, SiMe. The $^{29}Si$ NMR spectra had one peak at 15.56 ppm relative to tetramethylsilane.

That which is claimed is:

1. An alkoxyalkylalkenyl(3-chloro-2-alkylpropyl)silane.
2. The alkoxyalkylalkenyl(3-chloro-2-alkylpropyl)silane in accordance with claim 1 which is methoxymethylvinyl(3-chloro-2-methylpropyl)silane.
3. A chloroalkylalkenyl(3-chloro-2-alkylpropyl)silane.
4. The chloroalkylalkenyl(3-chloro-2-alkylpropyl)silane according to claim 3 which is chloromethylvinyl(3-chloro-2-methylpropyl)silane.

* * * * *